US008003406B2

(12) United States Patent
Muenke et al.

(10) Patent No.: US 8,003,406 B2
(45) Date of Patent: Aug. 23, 2011

(54) METHODS FOR DETECTING ATTENTION-DEFICIT/HYPERACTIVITY DISORDER

(75) Inventors: Maximilian Muenke, Bala Cynwyd, PA (US); Mauricio Arcos-Burgos, Rockville, MD (US); F. Xavier Castellanos, New York, NY (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 63 days.

(21) Appl. No.: 12/444,898

(22) PCT Filed: Sep. 27, 2007

(86) PCT No.: PCT/US2007/079616
§ 371 (c)(1),
(2), (4) Date: May 11, 2009

(87) PCT Pub. No.: WO2008/045687
PCT Pub. Date: Apr. 17, 2008

(65) Prior Publication Data
US 2010/0040626 A1 Feb. 18, 2010

Related U.S. Application Data

(60) Provisional application No. 60/850,972, filed on Oct. 11, 2006.

(51) Int. Cl.
*G01N 33/567* (2006.01)
*G01N 33/566* (2006.01)
*G01N 33/00* (2006.01)
*C12Q 1/68* (2006.01)

(52) U.S. Cl. .......... 436/504; 436/94; 436/501; 436/503; 435/6

(58) Field of Classification Search .................. None
See application file for complete search history.

(56) References Cited

U.S. PATENT DOCUMENTS

| | | |
|---|---|---|
| 2002/0045171 A1 | 4/2002 | Comings |
| 2004/0053257 A1 | 3/2004 | Kelsoe, Jr. et al. |
| 2004/0096847 A1 | 5/2004 | Murakami et al. |
| 2004/0235749 A1 | 11/2004 | Chemtob et al. |
| 2005/0019841 A1 | 1/2005 | Garman et al. |
| 2005/0043511 A1 | 2/2005 | Golz et al. |
| 2005/0048538 A1 | 3/2005 | Mignot et al. |
| 2005/0074808 A1 | 4/2005 | Vogeli et al. |
| 2005/0124569 A1 | 6/2005 | Guerciolini et al. |

FOREIGN PATENT DOCUMENTS
WO   WO 2004/018516 A1   3/2004

OTHER PUBLICATIONS

Anderson et al., "Effects of methylphenidate on functional magnetic resonance relaxometry of the cerebellar vermis in boys with ADHD," *Am. J. Psychiatry*, 159, 1322-1328 (2002).
Arcos-Burgos et al., "Attention-deficit/hyperactivity disorder in a population isolate: linkage to loci at 4q13.2, 5q33.3, 11q22, and 17p11," *Am. J. Genet.*, 75 (6), 998-1014 (2004).
Arcos-Burgos et al., "A Common Ancestral Haplotype Located at 4q13.2 Confers Susceptibility to ADHD," American Society of Human Genetics Conference, Program No. 158, Oct. 12, 2006 (abstract available on line on or after Sep. 12, 2006).
Biederman, "Attention-deficit hyperactivity disorder," *Lancet*, 366 (9481), 237-248 (2005).
Brookes et al., "The analysis of 51 genes in DSM-IV combined type attention deficit hyperactivity disorder: association signals in DRD4, DAT1 and 16 other genes," *Mol. Psychiatry.*, 11 (10), 934-953 (2006).
Castillo et al., "Correlation of myo-inositol levels and grading of cerebral astrocytomas," *AJNR Am. J. Neuroradiol.*, 21, 1645-1649 (2000).
Durrant et al., "Linkage disequilibrium mapping via cladistic analysis of single-nucleotide polymorphism haplotypes," *Am. J. Hum. Genet.*, 75 (1), 35-43 (2004).
Durrant et al., "Linkage disequilibrium mapping via cladistic analysis of phase-unknown genotypes and inferred haplotypes in the Genetic Analysis Workshop 14 simulated data," *BMC. Genet.*, 6 (Suppl 1), S100 (2005).
Horvath et al., "A discordant-sibship test for disequilibrium and linkage: no need for parental data," *Am. J. Hum. Genet.*, 63, 1886-1897 (1998).
Jain et al., "Epistatic Effect Between 11q22 and 17p11 for Attention-Deficit/Hyperactivity Disorder in the Paisa Genetic Isolate," American Society of Human Genetics Conference, Program No. 223, Oct. 13, 2006 (abstract available on line on or after Sep. 12, 2006).
Jin et al., "Striatal neuronal loss or dysfunction and choline rise in children with attention-deficit hyperactivity disorder: a 1H-magnetic resonance spectroscopy study," *Neurosci. Lett.*, 315 (1-2), 45-48 (2001).
Krain et al., "Brain development and ADHD," *Clin. Psychol. Rev.*, 26(4), 433-444 (2006).
Lake et al., "Family-based tests of association in the presence of linkage," *Am. J. Hum. Genet.*, 67 (6), 1515-1525 (2000). Lange et al., "On a general class of conditional tests for family-based association studies in genetics: the asymptotic distribution, the conditional power, and optimality considerations," *Genet. Epidemiol.*, 23 (2), 165-180 (2002).
Martin et al., "A test for linkage and association in general pedigrees: the pedigree disequilibrium test," *Am. J. Hum. Genet.*, 67 (1), 146-154 (2000).
Moore et al., "Differences in brain chemistry in children and adolescents with attention deficit hyperactivity disorder with and without comorbid bipolar disorder: a proton magnetic resonance spectroscopy study," *Am. J. Psychiatry*, 163 (2), 316-318 (2006).

(Continued)

*Primary Examiner* — Olga N Chernyshev
(74) *Attorney, Agent, or Firm* — Leydig, Voit & Mayer

(57) ABSTRACT

The invention provides a method of determining a susceptibility of a subject for development of ADHD. The method comprises obtaining a sample from the subject, analyzing the sample for an ADHD susceptibility haplotype of LPHN3 receptor which is associated with at least one genetic marker selected from the group consisting of rs7678046, rs1901223, rs6813183, and rs1355368, and determining if the subject has a susceptibility to develop ADHD, whereby the presence of the haplotype having one or more of the genetic markers is indicative of a susceptibility to develop ADHD. The invention also provides methods of treating ADHD.

12 Claims, 1 Drawing Sheet

OTHER PUBLICATIONS

Skol et al., "Joint analysis is more efficient than replication-based analysis for two-stage genome-wide association studies," *Nat. Genet.*, 38 (2), 209-213 (2006).

Sun et al., "Differences between attention-deficit disorder with and without hyperactivity: a $^1$H-magnetic resonance spectroscopy study," *Brain Dev.*, 27 (5), 340-344 (2005).

Yeo et al., "Developmental instability and working memory ability in children: a magnetic resonance spectroscopy investigation," *Dev. Neuropsychol.*, 17 (2), 143-159 (2000).

|  |  |  | rs7678046 |  |  | rs1901223 |  |  |  |  |  |  | rs6813183 | rs1355368 |  |  |  |  |  |
|---|---|---|---|---|---|---|---|---|---|---|---|---|---|---|---|---|---|---|---|
| Susceptibility Haplotype (SEQ ID NO. 1) | A | G | A | A | A | G | A | G | C | G | G | A | C | G | G | G | C | G | A |
| Protective Haplotype (SEQ ID NO. 2) | C | A | G | G | G | G | A | G | C | G | A | A | G | G | A | A | C | A | G |
| Consensus Human Genome Sequence (SEQ ID NO. 3) | A | A | G | G | G | G | T | G | G | G | A | G | A | G | G | G | A | G | A | A |

SEQUENCE LISTING

```
<160> NUMBER OF SEQ ID NOS: 3

<210> SEQ ID NO 1
<211> LENGTH: 23
<212> TYPE: DNA
<213> ORGANISM: Homo sapiens
```

```
<400> SEQUENCE: 1
agaaaaagag cgggagcggg cga                                           23

<210> SEQ ID NO 2
<211> LENGTH: 23
<212> TYPE: DNA
<213> ORGANISM: Homo sapiens

<400> SEQUENCE: 2
caggggggag cgaagggaaa cag                                           23

<210> SEQ ID NO 3
<211> LENGTH: 23
<212> TYPE: DNA
<213> ORGANISM: Homo sapiens

<400> SEQUENCE: 3
aaggggggtg ggagaggaga gaa                                           23
```

METHODS FOR DETECTING ATTENTION-DEFICIT/HYPERACTIVITY DISORDER

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 822 Byte ASCII (Text) file named "704363ST25.TXT," created on Feb. 2, 2009.

BACKGROUND OF THE INVENTION

Attention-Deficit/Hyperactivity Disorder (ADHD), the most common behavioral disorder of childhood, affects 8-12% of children worldwide. Biederman, Lancet, 366: 237-248 (2005). The disorder is defined as a persistent syndrome characterized by inattention, excessive motor activity, and impulsivity. Affected individuals are at increased risk for poor educational achievement, low income, underemployment, legal difficulties, and impaired social relationships. Faraone, J. Am. Acad. Child Adolesc. Psychiatry, 35: 1449-1459 (1996).

Genetic factors are implicated in the etiology of ADHD. Biederman, Lancet, 366: 237-248 (2005). For instance, the genetic locus 4q13.2 (i.e., the latrophilin 3 (LPHN3) genes,) has been reported as being associated with the development of ADHD. Arcos-Burgos, Am. J. Hum. Genet., 75: 998-1014 (2004). LPHN3 is a member of the LPHN subfamily of G-protein coupled receptors. Latrophilins have seven transmembrane regions as well as long N-terminal extracellular sequences containing a 19-amino acid signal peptide, a G-protein coupled receptor proteolytic site domain, and a serine/threonine-rich glycosylation region. LPHN3 is the most brain specific latrophilin. However, as of yet, a specific haplotype relating LPHN3 with a susceptibility of developing ADHD, has not been identified.

The foregoing shows that there exists a need for a method of determining a subject's susceptibility for developing ADHD. The present invention provides such a method. These and other objects and advantages of the invention, as well as additional inventive features, will be apparent from the description of the invention provided herein.

BRIEF SUMMARY OF THE INVENTION

The invention provides a method of determining whether a subject has a susceptibility for development of Attention Deficit Hyperactivity Disorder (ADHD). The method comprises obtaining a sample from the subject, analyzing the sample for an ADHD susceptibility haplotype of LPHN3 receptor by detecting nucleic acid in the sample that hybridizes with a sequence complementary to the ADHD susceptibility haplotype of LPHN3, where the ADHD susceptibility haplotype of LPHN3 receptor is associated with at least one genetic marker selected from the group consisting of rs7678046, rs1901223, rs6813183, and rs1355368, and determining if the subject has a susceptibility to develop ADHD, whereby the presence of the haplotype is indicative of susceptibility to develop ADHD.

The invention further provides a method of determining a susceptibility of a subject for development of ADHD. The method comprises measuring the NAA/Cr ratio by $^1$HMRS of subject's brain and correlating the NAA/Cr ratio with a number of copies of a susceptibility haplotype of LPHN3 in the subject.

In another embodiment, the invention provides a method of detecting whether a subject has a predisposition for developing ADHD. The method comprises screening a biological sample from a subject through in situ hybridization with the use of nucleic acid probes that are complimentary to at least one genetic polymorphism selected from the group consisting of rs7678046, rs1901223, rs6813183, and rs1355368.

In yet another embodiment, a method of collecting information on susceptibility for developing ADHD in a subject is provided. The method includes obtaining data on the presence or absence of a LPHN3 haplotype characterized by at least one genetic polymorphism selected from the group consisting of rs7678046, rs1901223, rs6813183, and rs1355368, and correlating the data obtained from the sample to a susceptibility haplotype of LPHN3.

Another embodiment of the invention provides a method of operating a PCR machine. The method comprises amplifying a nucleic acid sample suspected to contain a haplotype of LPHN3 associated with a susceptibility for developing ADHD, and collecting a signal from the sample that represents the presence of at least one genetic marker selected from the group consisting of rs7678046, rs1901223, rs6813183, and rs1355368.

The invention also provides a method of treating ADHD. The method comprises determining that a subject carries a haplotype of LPHN3 associated with a susceptibility of developing ADHD, and administering an effective amount of a composition comprising an LPHN3 receptor antagonist.

In another embodiment, the invention provides the use of an LPHN3 receptor antagonist in the manufacture of a medicament for the treatment of an ADHD patient who has been screened for a genetic polymorphism selected from the group consisting of rs7678046, rs1901223, rs6813183, and rs1355368.

BRIEF DESCRIPTION OF THE DRAWING

The FIGURE shows the sequences of the ADHD susceptibility haplotype of LPHN3 (SEQ ID NO: 1), the ADHD protective haplotype of LPHN3 (SEQ ID NO: 2), and the consensus human genome sequence of LPHN3 (SEQ ID NO: 3).

DETAILED DESCRIPTION OF THE INVENTION

The invention provides a method of determining whether a subject has a susceptibility for development of Attention Deficit Hyperactivity Disorder (ADHD). The method comprises obtaining a sample from the subject, analyzing the sample for an ADHD susceptibility haplotype of LPHN3 receptor by detecting nucleic acid in the sample that hybridizes with a sequence complementary to the ADHD susceptibility haplotype of LPHN3, where the ADHD susceptibility haplotype of LPHN3 receptor is associated with at least one genetic marker selected from the group consisting of rs7678046, rs1901223, rs6813183, and rs1355368, and determining if the subject has a susceptibility to develop ADHD, whereby the presence of the haplotype is indicative of susceptibility to develop ADHD.

It has been discovered that the LPHN3 gene (located on chromosome 4q13.2) and specifically, haplotypes having at least one of rs7678046, rs1901223, rs6813183, and rs1355368 markers are associated with susceptibility to developing ADHD. The susceptibility haplotype encompasses critical extracellular and transmembrane domains of LPHN3, a G-protein coupled receptor that is related to other G-protein coupled receptors DRD4 and DRD5, which are also directly associated with ADHD. LPHN3 is specifically expressed in brain regions of the mesolimbic system, which is associated with ADHD.

Single nucleotide variations in DNA sequences or single nucleotide polymorphisms (SNP) tend to be present in or close to genetic regions that are implicated in debilitating diseases. SNPs are also stably transferred from generation to generation and thus can be used as biomarkers in population studies. The study of SNPs is of great value for the medical and pharmaceutical communities as they can help predict disease association and how an individual may respond to a given drug. Human SNP genotyping has numerous implications in the context of medical significance of diseases, clinical diagnostics, improving current practice of medicine, and in drug discovery. Genetic markers rs7678046, rs1901223, rs6813183, and rs1355368 are SNPs, which together are associated with an ADHD susceptibility haplotype (i.e., an A-G-C-G variant), identified herein as SEQ ID NO: 1. There is a minimum critical region of ~327 Kb on chromosome 4q13.2 within the LPHN3 gene coding sequence, between exons 4 and 19, where the SNPs associated with the ADHD susceptibility haplotype occur. By way of contrast, it has been discovered that a protective haplotype exists, that is, a haplotype that appears to confer protection against developing ADHD, which is designated as SEQ ID NO: 2, and is an additional variant of the LPHN3 consensus human genome sequence (SEQ ID NO: 3).

Without wishing to be bound by any particular theory, the increased risk of developing ADHD in association with the susceptibility haplotype, appears to be consonant with the function of LPHN3 as a G-protein coupled receptor, with a plausible putative role in neuronal transmission and maintenance of neuron viability. It is thought that individuals carrying the susceptibility haplotype differ from other subjects who do not carry the susceptibility haplotype, in their N-acetylaspartate/creatine ratios (NAA/Cr) in the thalamus and cerebellar vermis, which suggests that LPHN3 variants differentially affect the metabolism of neural circuits implicated in ADHD pathophysiology. In fact, the dosage of the LPHN3 susceptibility haplotype varies inversely with the ratio of NAA/Cr, a measure of neuronal number known to be abnormal in ADHD. Data indicate that LPHN3 is strongly implicated in brain development, during which time, ADHD is considered to arise. Krain, *Clin. Psychol. Rev.* (2006). Therefore, one aspect of the invention provides a method of determining a susceptibility of a subject for development of ADHD by measuring the NAA/Cr ratio by $^1$HMRS of the subject's brain and correlating the NAA/Cr ratio with a number of copies of a susceptibility haplotype of LPHN3 in the subject.

For purposes of the present invention, the subject can be any mammal and can include, without limitation, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The sample may be may be any fluid or tissue obtained from the subject that contains the genetic sequence of the subject's LPHN3 gene. Preferred samples include brain tissue and blood.

The sample may be analyzed by any suitable method for determining the subject's LPHN3 gene sequence. For instance, one way of analyzing the sample is to amplify the genetic material contained in the sample using techniques known to those of skill in the art, such as PCR, and subsequently sequencing the sample to determine if the subject carries the ADHD susceptibility haplotype. Methods of gene sequencing are well known to those having ordinary skill in the art. Alternatively, the variant form of the LPHN3 receptor coded by the ADHD susceptibility LPHN3 haplotype, may be detected and analyzed in the sample. In this regard, labeled (i.e., radiolabeled or immunofluorescent labeled) or otherwise tagged anti-LPHN3 receptor antibodies, which are specific for the variant form of the LPHN3receptor, may be utilized. Such techniques are described more fully below and, additionally, are well known to those having ordinary skill in the art. Further, nucleic acid probes and arrays may be utilized. As SNPs constitute sites of variation flanked by regions of invariant sequence, their analysis requires no more than the determination and identity of the single nucleotide present at the site of variation and it is unnecessary to determine a complete gene sequence for each subject. Nucleic acid arrays are useful for SNP detection, as described for example, in U.S. Patent Nos. 5,981,956, 5,922,591, and 5,994,068. Arrays using DNA chips and tiled nucleic acid arrays, as well as additional methods of SNP detection, are described in U.S. Patent Publication No. 2003/0211500A1. Therefore, another embodiment of the invention provides a method of detecting whether a subject has a predisposition for developing ADHD. The method comprises screening a biological sample from a subject through in situ hybridization with the use of nucleic acid probes that are complimentary to at least one genetic polymorphism selected from the group consisting of rs7678046, rs1901223, rs6813183, and rs1355368.

In yet another embodiment, a method of collecting information on susceptibility for developing ADHD in a subject is provided. The method includes obtaining data on the presence or absence of a LPHN3 haplotype characterized by at least one genetic polymorphism selected from the group consisting of rs7678046, rs1901223, rs6813183, and rs1355368, and correlating the data obtained from the sample to a susceptibility haplotype of LPHN3.

Another embodiment of the invention provides a method of operating a PCR machine. The method comprising amplifying a nucleic acid sample suspected to contain a haplotype of LPHN3 associated with a susceptibility for developing ADHD; and collecting a signal from the sample that represents the presence of at least one genetic marker selected from the group consisting of rs7678046, rs1901223, rs6813183, and rs1355368.

The LPHN3 susceptibility haplotype status of ADHD subjects may predict responsiveness to therapeutic agents. Diagnosing subjects carrying the susceptibility haplotype for ADHD may allow a more individualized approach to the treatment of ADHD. Accordingly, methods of treatment are provided herein, which take advantage of the association between the LPHN3 haplotype and a susceptibility to develop ADHD. In one embodiment, a subject identified as carrying the ADHD susceptibility haplotype may be treated by utilizing LPHN3 gene silencing techniques with include LPHN3-specific siRNA or siNA, as described, for example, in U.S. Publication No. 2005/0124569, as well as antisense DNA and RNA.

The invention also provides a method of treating ADHD. The method comprises determining that a subject carries a haplotype of LPHN3 associated with a susceptibility of developing ADHD, and administering an effective amount of a composition comprising an LPHN3 receptor antagonist.

The term "antagonist" as used herein refers to any substance that counteracts the cellular effects of a natural compound. A "LPHN3 receptor antagonist," as used herein, means a compound that inhibits or blocks the activity of the LPHN3 receptor by interfering with the binding of the LPHN3 receptor with its natural ligand. LPHN3 receptor antagonists, thus, include molecules that bind to the LPHN3 receptor or its natural ligand in such a way as to interfere with the binding of the LPHN3 receptor to its natural ligand. As used herein, the terms "inhibit" and "block," as well as words stemming there from, do not necessarily imply a 100% or complete inhibition or blockage. Rather, there are varying degrees of inhibition or blockage of which one of ordinary skill in the art recognizes as having a potential benefit or therapeutic effect. In this regard, the LPHN3 receptor antagonist of the invention can achieve any level of inhibition or blockage of LPHN3 receptor inhibition. Any LPHN3 receptor antagonist may be used in conjunction with the invention. LPHN3 receptor antagonists include, for example, peptides, antibodies, and small molecules that bind to the LPHN3 receptor or its natural ligand. In this regard, peptides include peptide fragments, modified peptide fragments or pharmacologically acceptable salts of the LPHN3 receptor ligand as well analogues and derivatives thereof may be utilized to inhibit the LPHN3 receptor. Anti-LPHN3 receptor antibodies are known in the art. As used herein, the term "antibody" encompasses polyclonal antibodies, monoclonal antibodies, and functional antibody fragments.

One of ordinary skill in the art will readily appreciate that the antagonists of the present inventive methods can be modified in any number of ways, such that the therapeutic efficacy of the polypeptide or antagonist is increased through the modification. For instance, the antagonist could be conjugated either directly or indirectly through a linker to a targeting moiety. The practice of conjugating compounds, such as antagonists, to targeting moieties is known in the art. See, for instance, Wadwa et al., *J. Drug Targeting*, 3: 111 (1995), and U.S. Pat. No. 5,087,616. The term "targeting moiety" as used herein, refers to any molecule or agent that specifically recognizes and binds to a cell-surface receptor, such that the targeting moiety directs the delivery of the polypeptide or antagonist to a population of cells on which surface the receptor is expressed. Targeting moieties include, but are not limited to, antibodies, or fragments thereof, peptides, hormones, growth factors, cytokines, and any other naturally—or non-naturally-existing ligands, which bind to cell surface receptors. The term "linker" as used herein, refers to any agent or molecule that bridges antagonist to the targeting moiety. One of ordinary skill in the art recognizes that sites on the polypeptide or antagonist, which are not necessary for the function of the polypeptide or antagonist, are ideal sites for attaching a linker and/or a targeting moiety, provided that the linker and/or targeting moiety, once attached to the polypeptide or antagonist, do(es) not interfere with the function of the antagonist, i.e., the ability to inhibit the LPHN3 receptor.

In another embodiment, the invention provides the use of an LPHN3 receptor antagonist in the manufacture of a medicament for the treatment of ADHD a patient who has been screened for a genetic polymorphism selected from the group consisting of rs7678046, rs1901223, rs6813183, and rs1355368.

Pharmaceutical compositions or medicaments comprising a LPHN3 receptor antagonist are also contemplated in the invention. The carrier can be any suitable carrier. Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. It will be appreciated by one of ordinary skill in the art that, in addition to the following described pharmaceutical compositions, the polypeptides or any of the antagonists of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those ordinarily skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular polypeptide or antagonist, as well as by the particular method used to administer the polypeptide or antagonist. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One ordinarily skilled in the art will appreciate that these routes of administering the polypeptide or any of the antagonists of the present invention are known, and, although more than one route can be used to administer the polypeptide, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238 250 (1982), and ASHP Handbook on Injectable Drugs, Toissel, 4th ed., pages 622 630 (1986)).

Topical formulations are also well known to those of ordinary skill in the art. Such formulations are particularly suitable in the context of the present invention for application to the skin.

Formulations suitable for oral administration can consist of (a) liquid solutions, such as an effective amount of the antagonist dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compositions can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non pressured preparations, such as in a nebulizer or an atomizer. Such spray formulations also may be used to spray mucosa.

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The polypeptide or antagonists of the present invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5% to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compositions can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

Preferably, the compositions comprising the LPHN3 receptor antagonist described herein are administered orally, transmucosally, intravenously, or intraarterially. Of course, the LPHN3 receptor antagonist can be administered via the same or different routes.

Therefore, in one embodiment, a method of treating a subject carrying the ADHD susceptibility haplotype is provided. In said method, the subject is administered an effective amount of a pharmaceutical composition comprising one or more of the above described LPHN3 gene silencing agents or LPHN3 receptor antagonists.

The following examples further illustrate the invention but, of course, should not be construed as in any way limiting its scope.

EXAMPLES

The following materials and methods are used in all of the Examples unless otherwise noted.

Human subjects. Eighteen extended multigenerational families from a genetic isolate, the Paisa community of Colombia, which exhibits a high prevalence of ADHD are studied. The proposal to conduct the present study (Protocol #00-HG-0058), is jointly approved by the National Human Genome Research Institute Institutional Review Board and the Ethics Committee of the Universities of Antioquia, Würsburg, Trier, and Saarland. All adult participants provide written informed consent. Parents of participating minors provide written informed consent; minors age 5 and older who can write provide signed assent.

Northern blot analysis for determining LPHN3 expression in human brain. Northern blots (Human Brain MTN Blots II and V) is purchased from BD Biosciences (Palo Alto, Calif.). The LPHN3 probe is synthesized based upon its cDNA sequence at Invitrogen (Carlsbad, Calif.). A β-actin probe is used for normalization. Probes are labeled with $\gamma$-$^{32}$P-ATP (GE Healthcare, North Arlington Heights, Ill.) by T4 polynucleotide kinase (Invitrogen) and purified by QIAQUICK Nucleotide Removal Kit (Qiagen, Valencia, Calif.). Membranes are prehybridized with EXPRESSHYB (BD Biosciences, Rockville, Md.) for 1 h at 42° C. and hybridized with labeled probes for 3 h at 42° C. After hybridization, membranes are stringently washed and exposed on Kodak film at −70° C. for 10 days.

In situ hybridization analysis for identifying LPHN3 expression in human brain. Human brain tissue for in situ hybridization is obtained from the Brain and Tissue Bank for Developmental Disorders at the University of Maryland, Baltimore, Md. Analysis of brain tissues include amygdala, caudate nucleus, cerebellum, orbital frontal cortex, pontine nuclei, cingulated gyrus, occipital cortex and thalamus from male accident victims deceased at 2, 5, 8 and 30 years of age.

The antisense probe for LPHN3, a 362-bp amplicon within the final coding exon, is subcloned into BLUESCRIPT KS- (Stragene, San Diego, Calif.) and synthesized using a T3 primer. The in situ hybridization experiments are performed at Histoserve, Inc. (Germantown, Md.).

Immunohistochemical analysis for LPHN3 expression in human brain structures. Serial sections are taken from paraffin embedded tissue blocks for immunohistochemical examinations. For antigen retrieval, sections are treated with 0.01M sodium citrate buffer (pH 6.0) at 100° C. for 10 min. Sections are cooled at room temperature for 20 min and washed three times in PBS. Sections are then quenched for 20 min in a solution of 3 ml $H_2O_2$ and 180 ml methanol. After three washes in PBS, sections are incubated in 10% horse serum for 1 h. The LPHN3 primary antibody (1:500, Novus Biologicals, Littleton, Colo.) is diluted in 2% horse serum, and the sections are incubated in a humidified chamber at 4° C. overnight. The sections are incubated with secondary antibody for 1 h followed by avidin-biotin-complex incubation for 1 h and visualization with diaminobenzidine (DAB). The sections are counterstained with Mayer's hematoxylin for 10 min, dehydrated by grated ethanol washes of 95% and 100% and rinsed in xylene before being mounted.

Proton Magnetic Resonance Spectroscopy ($^1$H-MRS). To obtain measures of metabolic brain activity using $^1$H-MRS, T2-weighted high resolution anatomic images are obtained in the axial plane (TE=103 ms, TR=5910 ms, 3 mm slice thickness, and 5:27 (min:s) imaging time). Axial images are oriented parallel to the orbitomeatal anatomical reference plane. The T2-weighted images are used to guide multi-voxel MR spectroscopy volume selection. The 2D chemical shift imaging (CSI) point-resolved spectroscopic sequences (PRESS) technique (TE=30 ms, TR=1500 ms, NEX=3, resolution 10 nm×10 mm×10 mm, acquisition time=6:05) are localized in the inferior vermis using the anatomical reference images. 3D CSI PRESS sequence (TE=30 ms, TR=1500 ms, NEX=3, resolution 13.3 mm×13.3 mm×13.8 mm, acquisition time=10:23) explore the center of the brain including the striatum, thalamus, and the cingulate gyrus relative to anatomic images. Saturation bands around the 2D and 3D Volumes of Interest (VOI) are used to prevent contamination of the spectra from subcutaneous fat signal. All MR data are obtained on a 1.5 T Symphony Master Class Siemens Clinical Imaging System using an 8 channel head array coil. The spectra are transferred off-line to be processed automatically using LC Model. Provencher, NMR Biomed., 14: 260-264 (2001). For this initial analysis, focus is on the ratio of N-acetylaspartate (NAA) to creatine within each spectral voxel. Castillo, AJNR Am. J. Neuroradiol., 21: 1645-1649 (2000). Average data from voxels covering the left and right striatum (3-4 voxels), lateral (2 voxels) and medial (2 voxels) aspects of the thalamus, anterior (1 voxel) medial (1 voxel) and posterior (1 voxel) cingulate gyrus, and inferior vermis (2 voxels) are analyzed. Voxels containing cerebrospinal fluid are excluded from analyses. Criteria for acceptable reliability are those recommended by the LCModel provider. This multivoxel approach allows exploration of most of the structures linked to dysfunction of frontal-striatal-cerebellar circuits in ADHD. The imaged participants are neither sedated nor receiving medications for treatment of ADHD. Total scanning duration is 45 min. Absolute metabolite quantification is not attempted because of the requirement for markedly increased data acquisition time, which is particularly problematic for patients with ADHD. Presence of between group statistical differences of brain metabolites ratios are ascertained with the general linear model at an uncorrected two-tailed Alpha level of 0.05, since this was an exploratory analysis.

Linkage disequilibrium analyses. The Pedigree Disequilibrium Test (PDT) and its generalization is used to genotype-PDT (Geno-PDT) (Martin, Am. J. Hum. Genet., 67: 146-154 (2000); Martin, Genet. Epidemiol., 25: 203-213 (2003)) and FBAT (allele, haplotype, and genotype based) (Lange, Genet. Epidemiol., 23: 165-180 (2002); Horvath, Am. J. Hum. Genet., 63: 1886-1897 (1998); Lake, Am. J. Hun. Genet., 67: 1515-1525 (2000)), to search for evidence of linkage disequilibrium (LD) between ADHD and marker loci. PDT5.0 and UNPHASED software are used to estimate the Z statistic of PDT. Information about the theoretical basis of PDT and the power of this sample for PDT analyses has been described elsewhere. Arcos-Burgos, Mol. Psychiatry, 9: 252-259 (2004). Linkage disequilibrium via cladistic analysis is performed using CLADH. Durrant, BMC. Genet., 6 Suppl 1, S100 (2005); Durrant, Am. J. Hum. Genet., 75: 35-48 (2004). With this phytogenetic method, clades of haplotypes are tested for association with disease, exploiting the expected similarity of chromosomes with recent shared ancestry in the regions flanking the disease gene. CLADH haplotypes are reconstructed from the genealogies using MERLIN (Abecasis, Nat. Genet., 30: 97-101 (2002)) and SIMWALK2. Sobel, Amer. J. Hum. Genet., 58: 1323-1337 (1996). In general terms, both systems disclose similar haplotypes throughout the families. As controls, the haplotypes of 60 unaffected and unrelated individuals are selected from the genealogies.

Phylogenetic reconstruction. Alignment of sequences for 23 SNP markers reporting variations associated to ADHD are built using data from the UCSC genomic sequences for human consensus sequence, chimpanzee and the respective sequences for ADHD susceptibility and protective haplotypes. 1000 bootstrap replicates are generated for these sequences using the SEQBOOT module of the phylogeny inference package (PHYLIP) (ver. 3.2). Phylogenetic reconstruction is performed using the maximum likelihood method for DNA sequences under a Kimura two parameter mode of substitution with a 2:1 transitions:transvertions ratio. A consensus tree with bootstrap confidence levels is generated and plotted using TREEVIEW.

SNP detection using CEL1. Surveyor nuclease technology involves four steps: (i) PCR to amplify target DNA from both mutant and wild-type reference DNA; (ii) hybridization to form heteroduplexes between mutant and wild-type reference DNA; (iii) treatment of annealed DNA with Surveyor nuclease to cleave heteroduplexes; and (iv) analysis of digested DNA products using the detection/separation platform of choice. Unlabeled Surveyor nuclease digestion products are analyzed using conventional gel electrophoresis or high-performance liquid chromatography; end labeled digestion products are analyzed by automated gel or capillary electrophoresis. The technology detects rare mutants present at as low as 1 in 32 copies.

SNP detection using DHPLC. A total of 139 unrelated individuals with ADHD and 52 unrelated and unaffected controls from the U.S. population are studied. DNA extracted from blood is subject to PCR amplification of LPHN3 exons and intron-exon boundaries. DHPLC is performed on a WAVE 1100 DNA fragment analysis system (Transgenomics, Inc., Omaha, Nebr.). PCR products are denatured at 96° C. for 1 min, followed by gradual annealing to 65° C. over 30 min to form homo—and/or heteroduplexes. Products are automatically loaded on a DNA separation column and eluted according to manufacturer's instructions at a flow rate of 1.5 mL/min by mixing buffer A (0.11 mM TEAA) and buffer B (0.1 mM TEAA and 25% acetonitrile), with buffer B increasing 105 per min for 2.5 min. Samples were detected by a UV-C system. The oven temperatures for optimal heteroduplex separation under partial DNA denaturation are determined for each amplified fragment using the WAVE maker software (version 4.1). All samples are analyzed by visual inspection and those with variant peaks are sequenced. The nature and the position of each SNP is determined by direct sequencing using BigDye chemistry (Applied Biosystems, Foster City, Calif.) on the ABI 3100 Genetic Analyzer (Applied Biosystems, Foster City, Calif.) and the same primers used for DHPLC are used for sequencing. To be considered valid, SNPs are required to be observed in both strands sequenced.

SNP tagging. For SNP tagging a quality-based filter is employed, a second, population information-based filter (MAF, linkage disequilibrium blocks), and a third, biological significance-based filter (coding, expression modulating, splicing modulating, and accessing evolutionary conservation). Databases used for the selection are SNPdb (NCBI) and UCSC genome browser. Quality filtering is based on the information available through the SNP track of the UCSC genome browser and by using AB SNPbrowser 3.0. Customized LD blocks are defined using AB SNPbrowser 3.0 and Haploview. Biologic relevance is annotated on the UCSC genome browser with data available from UCSC (genome browser), NCBI (Entrez), and EBI (Ensembl). Conservation is based on MAF 8X conservation track (courtesy of Elliot Marguiles, NHGRI, NIH) and Exact Plus software (courtesy of Anthony Antonellis, NHGRI, NIH).

SNP genotyping and sequencing. Applied Biosystem's Big Dye Terminator Cycle Sequencing Ready Reaction Kits for direct cycle sequencing is used and reactions are run on an ABI Prism 3100 Genetic Analyzer. SNP rs10434219 genotyping is performed by RFLP analysis of the DraIII site created by the C variant. Genomic DNA is amplified by PCR, digested with DraIII, and analyze on 2% agarose gel. To perform SNP genotyping for rs4285117, rs2305339, rs734644, rs1397547, and rs1397548, Applied Biosystems SNAPSHOT Multiplex Kit is used according to manufacturer's directions. Briefly, genomic DNA is PCR amplified in a multiplex reaction with an annealing temperature of 48° C. and purified. SNAPSHOT reactions are performed with SNP-specific primers, and the reactions are run on an ABI Prism 3100 Genetic Analyzer.

Example 1

This example demonstrates the correlation between a particular haplotype of LPHN3 and ADHD.

Significant linkage of ADHD in 9 Paisa families is confirmed to the region on chromosome 4q13.2 (combined LOD=4.44) delineated by recombination events at D4S3248 and D4S1647. This suggests that a specific ADHD susceptibility factor occurs at 4q13.2 as a variant in this population.

To narrow the ~40 Mb minimal critical region, additional individuals in the linked families are ascertained and a second sample of nuclear families from the same genetic isolate (n=137) is investigated. A set of closely spaced (~50 Kb) SNP markers from the ILLUMINA panel is genotyped across the critical region. Both partitioned and joint analyses on the extended and nuclear pedigree sets are performed. Skol, *Nat. Genet.*, 38: 209-213 (2006). Tests of family-based association (i.e., allele, haplotype, and genotype) reveal a single marker-based area of association with ADHD at 62.4-62.7 Mb (UCSC coordinates); this area is located within the LPHN3 gene between markers rs1901223 and rs1355368.

Haplotype-based analyses corroborate the presence of the association, and disclose a ~327 Kb ADHD susceptibility haplotype embedded within LPHN3. This haplotype, shown in the FIGURE, constituted by SNP markers rs7678046, rs1901223, rs6813183, and rs1355368 (variant A-G-C-G, frequency 22.2%) is the most frequent haplotype and the only haplotype in the region conferring risk for ADHD (P<5.4× $10^{-4}$), with a relative risk of 4.2 (95% CI=1.77-9.99). The entire region encompassed by this haplotype also emerges as the only significantly (P<2.7×$10^{-5}$) associated susceptibility region, at ~62 Mb, based on cladistic analysis for linkage disequilibrium. Durant, *BMC Genet.*, 6 Suppl. 1, S100 (2005); Durrant, *Am. J. Hum. Genet.*, 75: 35-48 (2004).

The entire coding region of LPHN3 is sequenced in eight individuals carrying two (n=4), one (n=2), or zero (n=2) copies of the susceptibility haplotype. The analysis is not limited to the LPHN3 sequencing window to the shared haplotype region in order to include potential changes in regions regulating expression and/or alternative splicing. In these eight individuals, no mutations are identified in any exonic or intronic region. However, several additional SNPs show variation in these individuals, namely, rs4285117, rs10434219, rs9312082, rs12648576, rs2305339, rs734644, rs1397547, and rs1397548. Consequently, an additional 46 individuals from different families bearing the susceptibility haplotype are tested for potential mutations or polymorphisms at LPHN3 using SURVEYOR (Transgenomics, Omaha, Nebr.). The newly identified SNPs reveals that the ADHD susceptibility haplotype encompasses LPHN3 exons 4 through 19, coding for the olfactomedin, HR, gps, and transmembrane domains of the LPHN3 receptor, and containing the bulk of the variability conferred by splice isoforms. A systematic evaluation of every polymorphism detected is performed to determine potential functional effects at coding or regulatory regions. No polymorphisms meet criteria to be considered a mutation.

Additional genotyping is conducted on Paisa as well as 184 U.S. families using 49 tagged SNPs distributed evenly over the LPHN3 gene with a resolution of ~5.8 Kb. Three main linkage disequilibrium (LD) blocks emerge, with structures resembling those described for the HAPMAP's CEPH population. A subset of 23 SNP markers discloses association and linkage of the LPHN3 region with the ADHD phenotype. Within each population, as well as in the pooled population, every block of LD contains susceptibility and protective haplotypes associated with the ADHD phenotype. Haplotype reconstruction involving 23 associated markers identifies an extended haplotype conferring susceptibility to ADHD (pooled frequency 6%) and a distinct haplotype conferring protection from ADHD (2%). Within this extended haplotype is immersed the original A-G-C-G variant (markers rs7678046, rs1901223, rs6813183, and rs1355368). A phylogenetic reconstruction, using the 23 markers of the susceptibility haplotype and the corresponding UCSC genomic sequence of chimpanzee as an out-group, reveals several homologies, suggesting that the ADHD susceptibility haplotype is the ancestral haplotype from which the ADHD protective haplotype evolved.

Next, expression of LPHN3 is evaluated. Northern blot analysis shows significant expression of LPHN3 mRNA in human amygdala, caudate nucleus, cerebellum, and cerebral cortex. Formalin-fixed tissues of brain regions from humans of different ages are examined for LPHN3 expression by in situ hybridization. There is a consistent, strong cytoplasmic signal in neurons of the amygdala, caudate nucleus, pontine nucleus and in Purkinje cells of the cerebellum at all ages tested (i.e., at 2, 5, 8, and 30 years). Involvement of the prefrontal cortex, cerebellum, amygdala, and temporal lobes is implicated in ADHD. Weak cytoplasmic signals for LPHN3 are observed in a subset of cingulate gyrus neurons in the 2 and 5 year olds, but not in the 8 and 30 year olds, and in induisium griseum neurons in the 2 year old. The orbital frontal cortex, occipital cortex, and thalamus show no LPHN3 expression at any age. Areas of brain that reveal LPHN3 expression by in situ hybridization are also consistently immunoreactive using anti-LPHN3 antibody. Further, a panel of normal human pooled cDNAs (BD Biosciences-Clontech, CA) reveals robust expression of a single 3.7 Kb LPHN3 mplicon (primers covering the whole open reading frame) in cerebellum, cerebral cortex, thalamus, amygdala, substantia nigra, hippocampus, spinal cord, and retina. Expression in fetal brain is more pronounced than in whole postnatal brain. Fibroblasts and testes also show notable expression. Minimal expression is detected in thymus, lung, prostate, ovaries, heart, pancreas, liver, and kidney. No expression is detected in cDNA from leucocytes, spleen, skeletal muscle, colon, small intestine, and placenta.

This study confirms the association between a LPHN3 haplotype characterized by markers rs7678046, rs1901223, rs6813183, and rs1355368, and ADHD.

Example 2

This example demonstrates biochemical changes associated with the ADHD susceptibility haplotype of LPHN3.

The potential differences between carriers and noncarriers of the susceptibility haplotype with respect to brain metabolism, is assessed by the ratio of N-acetylaspartate (NAA) to creatine (Cr). This ratio, determined using proton magnetic resonance spectroscopy ($^1$H-MRS), provides an index of neuronal number or viability, and has been shown to be decreased in ADHD. Moore, *Am. J. Psychiatry*, 163: 316-318 (2006); Sun, *Brain Dev.*, 27: 340-344 (2005), Yeo, *Dev. Neuropsychol.*, 17: 143-159 (2000); Jin, *Neurosci. Lett.*, 315: 45-48 (2001). Certain target regions are chosen (striatum, cingulated gyrus, cerebellar vermis) based on prior evidence of anatomic abnormalities and an added region that has been difficult to quantify volumetrically, i.e., the medial and lateral thalamus. $^1$H-MRS is performed on 15 individuals carrying the ADHD susceptibility haplotype (two unaffected with ADHD), and 8 individuals carrying the ADHD protective haplotype (one affected with ADHD), and 8 control individuals with other haplotype variants differing from the susceptibility and protective haplotypes (all unaffected). Multivariate general linear model analyses is used incorporating the effects of sex and carrier and affected status; age is considered as a covariate. Across all individuals carrying the susceptibility haplotype, NAA/Cr is significantly decreased in the left lateral thalamus ($p<0.01$), left medial thalamus ($p<0.05$), and the right striatum ($p<0.05$), and significantly increased in the inferior-posterior cerebellar vermis ($p<0.05$). The increased NAA/Cr ratio in the vermis may reflect a greater steady state blood flow to the vermis, which is normalized by methylphenidate, a treatment for ADHD. Anderson, *Am. J. Psychiatry*, 159: 1322-1328 (2002).

In order to control for the effect of ADHD status, we examine the effect of the number of copies of the susceptibility and protective haplotype on the NAA/Cr ratio. The NAA/Cr ratio is increased monotonically in the right medial and lateral thalamus in relation to the number of copies of the susceptibility haplotype. Carriers of two copies of the susceptibility haplotype have the lowest levels of NAA/Cr; the ratio increases in a dosage-dependent fashion, reaching the highest levels in individuals with two copies of the protective haplotype and in controls ($p<0.05$).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of aiding a determination of whether a subject has a susceptibility for development of Attention Deficit Hyperactivity Disorder (ADHD), the method comprising
   a) obtaining a sample from the subject,
   b) analyzing the sample for an ADHD susceptibility haplotype of latrophilin 3 receptor gene (LPHN3) by detecting nucleic acid in the sample with a sequence comprising at least one genetic marker selected from the group consisting of the rs7678046, rs 1901223, rs6813183, and rs 1355368 polymorphisms associated with the ADHD susceptibility haplotype of LPHN3 receptor, wherein rs7678046 refers to (i) an adenosine at nucleotide position 5 in SEQ ID NO: 1 within the subject's LPHN3 locus or (ii) a thymine on the complementary strand at the position complementary to the adenosine at position 5, wherein rs1901223 refers to (i) a guanine at nucleotide position 8 in SEQ ID NO:1 within the subject's LPHN3 locus or (ii) a cytosine on the complementary strand at the position that is complementary to the guanine at position 8, wherein rs6813183 refers to (i) a cytosine at nucleotide position 17 in SEQ ID NO: 1 within the subject's LPHN3 locus or (ii) a guanine on the complementary strand at the position that is complementary to the cytosine at position 17, and wherein rs1355368 refers to (i) a guanine at nucleotide position 18 in SEQ ID NO:1 within the subject's LPHN3 locus or (ii) a cytosine on the complementary strand at the position that is complementary to the guanine at position 18; and
   c) determining if the subject has a susceptibility to develop ADHD, whereby the presence of the haplotype is indicative of susceptibility to develop ADHD.

2. The method of claim 1, wherein the detected nucleic acid in the sample has a sequence comprising rs7678046.

3. The method of claim 1, wherein the detected nucleic acid in the sample has a sequence comprising rs1901223.

4. The method of claim 1, wherein the detected nucleic acid in the sample has a sequence comprising rs6813183.

5. The method of claim 1, wherein the detected nucleic acid in the sample has a sequence comprising rs1355368.

6. The method of claim 1, wherein the detected nucleic acid in the sample has a sequence comprising rs7678046, rs1901223, rs6813183, and rs1355368.

7. The method of claim 1, wherein the sample is a tissue.

8. The method of claim 1, wherein the sample is blood.

9. The method of claim 1, wherein the subject's genome comprises a number of copies of the ADHD susceptibility haplotype and the method comprises determining the number of copies of the ADHD susceptibility haplotype carried by the subject.

10. The method of claim 6, wherein the detected nucleic acid in the sample has a sequence comprising SEQ ID NO:1 or its complement.

11. A method of aiding a determination of whether a subject has a susceptibility for development of ADHD, the method comprising
   a) obtaining a biological sample from the subject,
   b) screening the sample for a haplotype of latrophilin 3 receptor gene (LPHN3) by in situ hybridization with one or more nucleic acid probes, wherein one or more probes are complimentary to at least one of the genetic polymorphisms selected from the group consisting of rs7678046, rs1901223, rs6813183, and rs1355368 wherein rs7678046 refers to (i) an adenosine at nucleotide position 5 in SEQ ID NO: 1 within the subject's LPHN3 locus or (ii) a thymine on the complementary strand at the position complementary to the adenosine at position 5, wherein rs1901223 refers to (i) a guanine at nucleotide position 8 in SEQ ID NO:1 within the subject's LPHN3 locus or (ii) a cytosine on the complementary strand at the position that is complementary to the guanine at position 8, wherein rs6813183 refers to (i) a cytosine at nucleotide position 17 in SEQ ID NO: 1 within the subject's LPHN3 locus or (ii) a guanine on the complementary strand at the position that is complementary to the cytosine at position 17, and wherein rs1355368 refers to (i) a guanine at nucleotide position 18 in SEQ ID NO:1 within the subject's LPHN3 locus or (ii) a cytosine on the complementary strand at the position that is complementary to the guanine at position 18; and c) determining if the subject has a susceptibility for development of ADHD, whereby detecting the presence of the LPHN3 haplotype with one or more nucleic acid probes is indicative of a susceptibility for development of ADHD.

12. The method of claim 11, wherein the method comprises using probes complementary to the genetic polymorphisms rs7678046, rs1901223, rs6813183, and rs1355368.

* * * * *